(12) United States Patent
Mönnich

(10) Patent No.: US 10,800,034 B2
(45) Date of Patent: Oct. 13, 2020

(54) METHOD FOR TRACKING A HAND-GUIDED ROBOT, HAND-GUIDED ROBOT, COMPUTER PROGRAM, AND ELECTRONICALLY READABLE STORAGE MEDIUM

(71) Applicant: Siemens Healthcare GmbH, Erlangen (DE)

(72) Inventor: Holger Mönnich, Friedberg (DE)

(73) Assignee: Siemens Healthcare GmbH, Erlangen (DE)

(*) Notice: Subject to any disclaimer, the term of this patent is extended or adjusted under 35 U.S.C. 154(b) by 215 days.

(21) Appl. No.: 16/103,129

(22) Filed: Aug. 14, 2018

(65) Prior Publication Data

US 2019/0054618 A1  Feb. 21, 2019

(30) Foreign Application Priority Data

Aug. 17, 2017 (EP) ..................................... 17186595

(51) Int. Cl.
| | |
|---|---|
| *B25J 9/16* | (2006.01) |
| *B25J 1/02* | (2006.01) |
| *B25J 11/00* | (2006.01) |
| *A61B 34/30* | (2016.01) |
| *A61B 18/14* | (2006.01) |

(52) U.S. Cl.
CPC ............... *B25J 9/163* (2013.01); *A61B 34/30* (2016.02); *B25J 1/02* (2013.01); *B25J 9/1633* (2013.01); *B25J 9/1664* (2013.01); *B25J 9/1694* (2013.01); *B25J 11/008* (2013.01); *A61B 18/14* (2013.01); *G05B 2219/39325* (2013.01)

(58) Field of Classification Search
None
See application file for complete search history.

(56) References Cited

U.S. PATENT DOCUMENTS

| | | | |
|---|---|---|---|
| 2016/0221189 A1 | 8/2016 | Nilsson et al. | |
| 2016/0296296 A1 | 10/2016 | Bowling et al. | |

FOREIGN PATENT DOCUMENTS

| | | |
|---|---|---|
| DE | 102007017578 A1 | 10/2008 |
| EP | 1815950 A1 | 8/2007 |
| EP | 1915963 A1 | 4/2008 |

OTHER PUBLICATIONS

European Search Report for corresponding Application No. 17186595.9-1205, dated Feb. 26, 2018.

*Primary Examiner* — Bhavesh V Amin
(74) *Attorney, Agent, or Firm* — Lempia Summerfield Katz LLC

(57) ABSTRACT

A method is provided for tracking a hand-guided robot including a control unit and at least one manipulator coupled to an end effector, in which the manipulator includes a plurality of joints and links and the end effector is manually displaceable within an operational volume. In the method, the control unit determines at least one movement information of each joint during and/or after a manual or partially manual displacement of the end effector, and a position and orientation information of the end effector inside the operational volume during and/or after the displacement of the end effector using the determined movement information of each joint and a software-based kinematic and dynamic model of the manipulator stored in a memory of the control unit.

16 Claims, 3 Drawing Sheets

METHOD FOR TRACKING A HAND-GUIDED ROBOT, HAND-GUIDED ROBOT, COMPUTER PROGRAM, AND ELECTRONICALLY READABLE STORAGE MEDIUM

The application claims the benefit of European Patent Application No. EP 17186595.9, filed Aug. 17, 2017, which is hereby incorporated by reference in its entirety.

TECHNICAL FIELD

The disclosure relates to a method for tracking a hand-guided robot including a control unit and at least one manipulator coupled to an end effector, in which the manipulator includes a plurality of joints and links and the end effector is manually displaceable within an operational volume. The disclosure further relates to a hand-guided robot, a computer program, and an electronically readable storage medium.

BACKGROUND

Hand-guided robots may be used in medicine for performing minimally invasive interventions on a patient. The robot is manually actuated and controlled by a physician performing the intervention. A medical instrument or a member is attached as end effector to the hand-guided robot. By tracking of the robot movement, the current position of the end effector may be determined to survey the intervention. As the accuracy and the precision of the tracking is directly related to the accuracy and the precision of the performed intervention, it is desirable that the position and orientation of the member used for the intervention may be determined as accurate and precise as possible.

SUMMARY AND DESCRIPTION

Therefore, the object of the disclosure is to provide a method which allows an accurate and precise tracking of a hand-guided robot.

The scope of the present disclosure is defined solely by the appended claims and is not affected to any degree by the statements within this description. The present embodiments may obviate one or more of the drawbacks or limitations in the related art.

This object is achieved in a method as initially described by the control unit determining at least one movement information of each joint during and/or after a manual or partially manual displacement of the end effector, and a position and orientation information of the end effector inside the operational volume during and/or after the displacement of the end effector using the determined movement information of each joint and a software-based kinematic and dynamic model of the manipulator stored in a memory of the control unit.

The advantage of the solution is the improvement of the absolute accuracy of the tracking of the hand-guided robot. The hand-guided robot includes a manipulator, e.g., in the form of a robot arm. The manipulator is fixed with one end at a defined position, and at the other end of the manipulator an end effector is coupled to or attached to the manipulator. The manipulator includes a plurality of joints and links, in which the joints are adjustable and the links are rigid. A link may be arranged between two neighboring joints of the manipulator. The end effector coupled to the manipulator is movable within the operational volume, which includes all points in space to which the end effector may be displaced during hand-guiding. A displacement of the end effector within the operational volume may occur by a manual displacement of the end effector, performed, for example, by an operator of the hand-guided robot. As the end effector is coupled to the manipulator, a movement of the manipulator is induced during the manual displacement of the end effector. The links of the manipulator are stiff, so that the movement of the manipulator causes mainly a movement of the joints, which may be deflectable, pivotable, and/or rotatable. It may be provided that one or more joints may be actuated automatically, whereas the other joints of the manipulator are moved by the manual displacement of the end effector resulting in a partially manual displacement. It is also possible that the hand-guiding of the robot occurs indirectly by an operator actuating the joints of a robot using a respective control element, e.g., a joystick or a keyboard. The input commands of the operator on the control elements generate control signals which cause a movement of the joints and therefore a displacement of the end effector. The manipulator may have three translational degrees of freedom and three rotational degrees of freedom to obtain a high flexibility for displacement.

During and/or after a manual or partially manual displacement of the end effector, at least one movement information is determined for each joint of the manipulator by a control unit of the hand-guided robot. In a memory of the control unit, a software-based kinematic and dynamic model of the manipulator is stored. This model describes the kinematics and the dynamics of the manipulator using both its exact geometry and a physical model describing the mechanical properties of one or more of the end effector, the joints, or the links of the manipulator. Based on this model, the absolute position of the end effector inside the operational volume may be determined by using the movement information determined for each joint during and/or after a displacement of the end effector.

The kinematic and dynamic model may be a so-called absolutely accurate model. Such models are known in the state of the art but are used for accurately controlling the automatically actuated robot, like, for example, described in German Patent Publication DE 10 2007 017 578 A1 for an industrial robot. The basic idea is, deviating from the use in controlling the robot, to use an absolutely accurate model to track the position of the end effector with a very high precision, (e.g., as needed in medical interventions). In other words, the application of the model is sort of inverted from using it to automatically move to a position with high precision to using it to derive a position which has been chosen manually with a high precision.

The movement information of a joint may include an information on one or more of a rotational movement of the joint, a translational movement of the joint, a torque applied to the joint, or a force applied to the joint. The movement information may be measured using sensors at or in the joint, which measure any angular, rotational, and/or translational movement on the joint. Additionally, or alternatively, one or more sensors which measure a torque applied to the joint and/or on a force applied to the joint may be utilized for the determination of the movement information. It may be provided that the joints of the manipulator are coupled to motors and/or gears that allow an automatic or partially automatic actuation of the manipulator. In such a case, it is also possible that the movement information for the joints is determined by evaluating a movement of the motors and/or the gears, e.g., by the joints, which are not actuated automatically. During the manual displacement of the end effector or the manipulator, respectively, a movement of the motors and/or gears provided for an automatic actuation and/or for an indirect hand-guiding is induced because the motors and/or gears are coupled to the respective joints. Based on this movement information, the position and orientation information of the end effector may be calculated using the kinematic and dynamic model of the manipulator. As one end of the manipulator is fixed at a defined position within the operational volume, the relative change of the position of the end effector to this defined position and therefore the absolute position of the end effector depends on the movement of the joints. It is also possible that control signals used for an automatic actuation of one or more joints and/or control signals generated during an indirect hand-guiding using a control element are evaluated for obtaining a movement information of the respectively actuated joints.

In one embodiment, the kinematic and dynamic model describes the geometry of the manipulator and at least one property of at least one joint and/or link of the manipulator, in which the at least one property includes one or more of the following: friction of a joint, flexibility of a joint, hysteresis of a joint, backlash of a joint, or elasticity of a link. All of the joints of the manipulator may be described in the model. It is possible that additional physical properties like an elasticity of the links is described in the model as well to account for the effect of torques and/or forces applied to the joints, in particular gravitational forces. However, a description of the links may be neglected if the influence, (e.g., of the flexibility), is negligible compared to the influence of the joints. These properties of the joints may describe effects that influence the position and orientation of the end effector dependent on torques and/or forces applied to the respective joints. Such effects may be static friction, dynamic friction, the flexibility of a joint, a hysteresis of the joint occurring upon a subsequent forward and backward movement of the joint, and/or a backlash of a joint which may describe a threshold for a minimum torque or force that is required to induce a movement of the joint.

In an embodiment, a control unit may determine a displacement trajectory of the end effector during displacement by determining the position and orientation information at different points in time during displacement. The determined position and orientation information at each point in time may be stored in a memory of the control unit. Based on this information, the displacement trajectory may be determined describing the path of the end effector in the operational volume. The frequency in which the position and orientation information is determined influences the temporal and/or spatial resolution of the displacement trajectory.

Additionally, the control unit may calculate, at each point in time, a deviation information respectively describing the deviation between the displacement trajectory and a target trajectory which is stored in the memory of the control unit. The target trajectory may be a trajectory for the displacement of the end effector which may have been planned earlier, e.g., in the case of a medical minimally invasive intervention. It may be stored prior to the manual displacement of the end effector in the memory of the control unit. The deviation information describes the difference between the displacement trajectory and the target trajectory and is therefore a measure to determine the distance of the current position of the end effector to an optimal or a desired position, which is described by the target trajectory. Besides the position, the orientation of the end effector may also be described by the target trajectory, so that also a deviation of the current orientation of the end effector compared to the target trajectory may be determined.

One or more of deviation information, the displacement trajectory, or the target trajectory may be displayed on a screen connected to the control unit and/or transferable via an interface unit of the control unit to at least one peripheral device. Both the target trajectory and the displacement trajectory may be depicted on the screen. An operator of the hand-guided robot may therefore see both trajectories, which facilitates the manual displacement of the end effector alongside the target trajectory. Also, the deviation information may be displayed on the screen by giving the distances in predefined directions between the displacement trajectory and the target trajectory and/or an angular misalignment of the current orientation of the end effector compared to the orientation provided by the target trajectory. One or more of the deviation information, the displacement trajectory, or the target trajectory may be transferred via an interface unit to one or more peripheral devices such as a computer, a data storage, and/or a medical imaging apparatus.

Additionally, an image data set of a workpiece or a patient may be displayed on the screen. The image data set of the workpiece or the patient may be provided by an imaging apparatus, (e.g., an X-ray apparatus, a computer tomography apparatus, or a magnetic resonance tomography apparatus). The image data set may be registered to a coordinate system, in which the position of the hand-guided robot, or the end effector, respectively, within the operational volume is determined. In particular, the coordinate systems used for tracking may be registered to the coordinate system of the image data set. This may be achieved by using markers at defined positions in the operational volume during the imaging procedure and/or by using a mutual coordinate system for both imaging and tracking of the robot. Therefore, a calibration may be performed for the hand-guided robot and/or the imaging apparatus prior to an intervention, in particular, if both the imaging device with which the image data set was acquired or with which the image data set may be registered and the robot are part of the same interventional arrangement, (e.g., positioned in an operating room for a patient).

It is both possible to display an image data set on the screen which has been recorded prior to the movement of the hand-guided robot or to display a current and/or frequently updated image data set recorded during the procedure. In an advantageous manner, the operator of the hand-guided robot may see both workpiece and/or the patient on a screen as well as the target trajectory for the end effector, the displacement trajectory of the end effector, and the respective deviation information overlaid thereon. This enables a precise and controllable manual displacement of the end effector towards and/or inside the workpiece or the patient. A three-dimensional pre-interventional image data set of a patient may also be used for planning of the target trajectory prior to an intervention and/or updated image data sets may be used for a correction or adaption of the target trajectory during an intervention. Image data sets showing the current situation and the position of the end effector may also be used to make plausible the position and orientation information of the end effector as determined in the kinematic and dynamic model.

In certain embodiments, the control unit may calculate an error information for each determined position and orientation information based on the kinematic and dynamic model. Such a calculation may be based on correction factors and/or tolerances for an individual manipulator that may occur due to tolerances during fabrication. It is also possible to account for a misalignment of axis or for axis offsets when a coordinate system is used. By using the kinematic and dynamic model, the control unit may calculate an error information for each determined position and orientation information describing a possible deviation of the determined position and orientation information from the real position and orientation of the end effector.

The error information may be displayed on a screen connected to the control unit and/or transferable via an interface unit of the control unit to at least one peripheral device. The error information may be displayed on the screen additionally to a deviation information and/or a displacement trajectory and/or a target trajectory. Based on the error information, an operator of the hand-guided robot is able to determine a volume in which the end effector is positioned and oriented. Additionally, or alternatively, the error information may be transferred via an interface unit of the control unit to a peripheral device like a computer, a display device for displaying or visualizing the error information, and/or a device for storing the error information.

In certain embodiments, a biopsy needle, an ablation electrode, or an endoscope may be used as end effector and/or a medical minimally invasive intervention on a patient may be surveyed. The position and orientation information of the end effector may describe the position and orientation of the tip of a biopsy needle, or the electrically active area of an ablation electrode or the position of an image data acquisition unit of an endoscope. In a minimally invasive intervention on a human or animal patient, it is especially advantageous to precisely track a position and orientation of the utilized end effector prior and during insertion into the patient, which may be required to be performed manually.

In certain embodiments, a serial arm robot with at least six joints and six degrees of freedom may be used as the hand-guided robot. A serial arm robot including a manipulator with six or more joints providing six degrees of freedom is movable flexibly to any position within the respective operational volume. Therefore, any position or trajectory inside the physical range of the manipulator may be targeted for a displacement of the hand-guided robot.

An embodiment of the hand-guided robot may provide that the hand-guided robot includes a control device configured to perform a method. All remarks regarding the method also apply to the hand-guided robot.

A computer program may include instructions which, when the program is executed by a computer, cause the computer to carry out a method. The computer may be the control unit of a hand-guided robot and/or a peripheral computer which is configured to control the hand-guided robot additionally or alternatively to the control unit of the hand-guided robot.

An electronically readable storage medium has a computer program stored thereon.

BRIEF DESCRIPTION OF THE DRAWINGS

Additional advantages and features of the disclosure become evident from the embodiments discussed below as well as from the figures.

DETAILED DESCRIPTION

Figure 1:
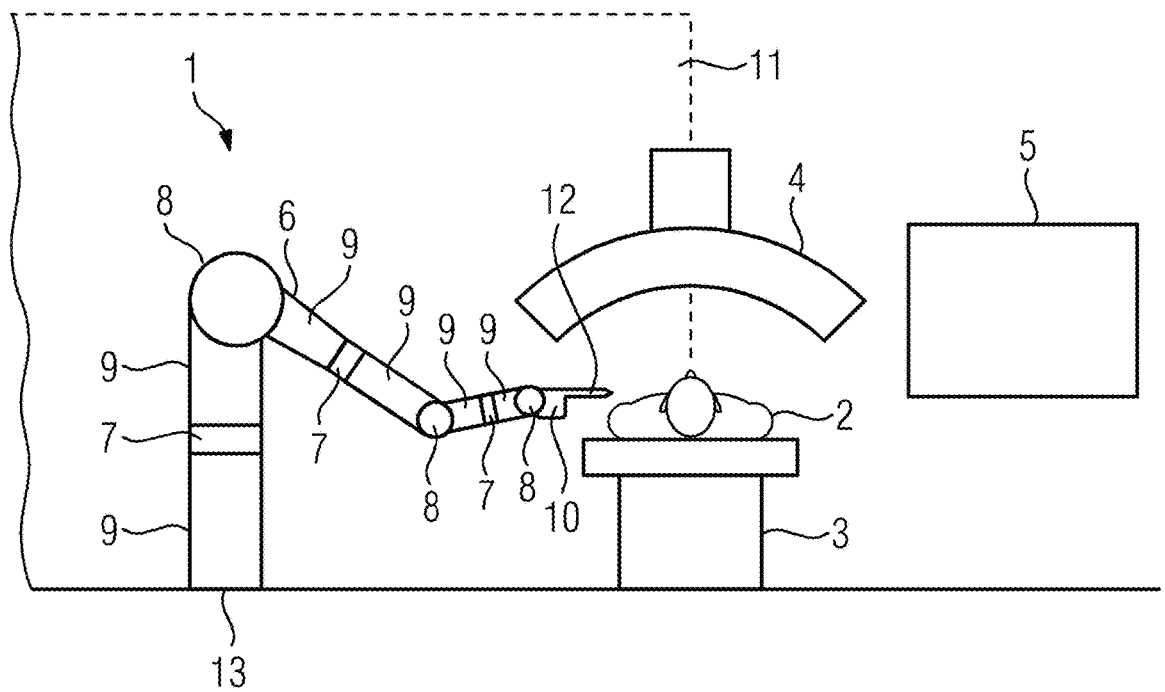
FIG. 1 depicts a schematic view of an exemplary arrangement including a hand-guided robot for a medical minimally invasive intervention.

In FIG. 1, a schematic view of an arrangement including a hand-guided robot 1, a patient 2 on a table 3, an X-ray apparatus 4, and a screen 5 is shown. The hand-guided robot 1 includes a manipulator 6, wherein the manipulator contains a plurality of joints 7, 8 and links 9 as well as an end effector 10. The joints 7 allow a rotational movement of the manipulator and the joints 8 are pivotable allowing the manipulator to be moved in certain angles. The end effector 10 of the hand-guided robot 1 is displaceable within the operational volume 11. The depiction of the hand-guided robot 1 is schematically and is not necessarily in scale to the patient, as smaller hand-guided robots 1 with smaller operational volume 11 are within the scope of the disclosure.

The end effector 10 of the hand-guided robot 1 is manually displaceable within the operational volume 11. During manual displacement, the position and the orientation of the end effector or a tip 12 of the end effector, respectively, is tracked. The end effector may be a biopsy needle, an ablation electrode, or an endoscope. The end effector 10 may be used for a medical minimally invasive intervention on the patient 2. A manual displacement of the end effector 10 causes a movement of the joints 7, 8. As one end 13 of the hand-guided robot 1 is immobilized in a defined position within the operational volume 11, the position and orientation of the end effector 10 or the tip 12 of the end effector, respectively, may be determined from the movement information for each joint 7, 8 by using a kinematic and dynamic model of the manipulator. It is also possible that a hand-guiding of the robot 1 occurs by an automatic actuation of the joints 7, 8 which is induced by an operator generating respective control signals by using an operating element like, for instance, a joystick.

Using the X-ray apparatus 4, image data sets of the patient 2 may be recorded prior and/or during the intervention. Therefore, the image data sets and the tracking of the hand-guided robot 1 may use registered coordinate system allowing to fuse the image data and the position and orientation information of the tracking. On the screen 5, the image data sets and/or the position and orientation information may be displayed alongside with other information, as described in the following.

Figure 2:
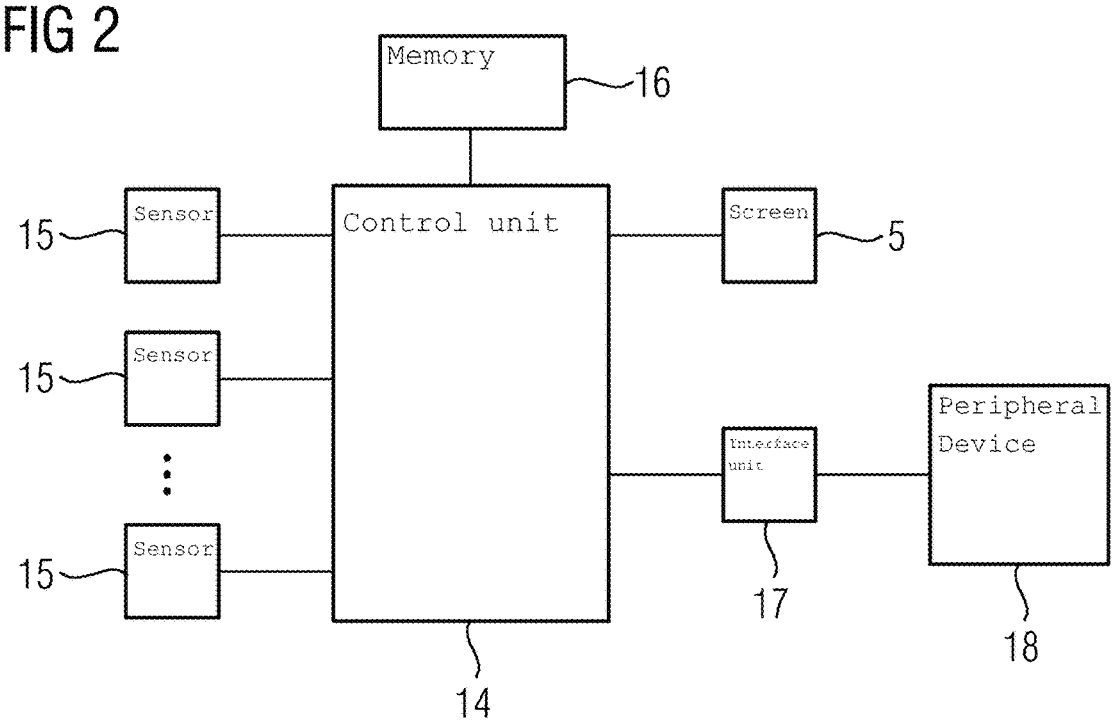
FIG. 2 depicts a schematic block diagram of a hand-guided robot according to an embodiment.

In FIG. 2, a schematic block diagram of a hand-guided robot 1 is shown. The hand-guided robot 1 includes a control unit 14, which includes a memory 16 in which the software-based kinematic and dynamic model of the manipulator 6 including the end effector 10 is stored. The kinematic and dynamic model is an absolutely accurate model, which, in this case, is not used for controlling movement of the hand-guided robot 1 to a certain position, but to precisely track the end effector on manually induced movement. For each joint 7, 8 at least one property is described in the model, wherein the properties may include the friction of the joint, the flexibility of a joint, the hysteresis of the joint, or the backlash of a joint. Additionally, it is possible that also one or more properties for each link 9 is described in the kinematic and dynamic model. A property of a link 9 may be an elasticity of a link 9.

The hand-guided robot 1 may additionally include a plurality of sensors 15 configured to measure a movement information for a respective joint 7, 8 of the hand-guided robot 1. Each of the joints 7, 8 may be assigned a sensor 15, so that for each joint 7, 8 a movement information may be obtained. The movement information may include an information on one or more of a rotational movement of the joint, a translational movement of the joint, a torque applied to the joint, or a force applied to the joint. After and/or during a manual or a partially manual displacement of the end effector 10, the control unit 14 calculates a position and orientation information of the end effector 10. The position and orientation information of the end effector 10 is calculated using the movement information of each joint 7, 8 measured by the sensors 15 as well as the kinematic and dynamic model of the manipulator that is stored in a memory 16 of the control unit 14. It is possible that during the displacement of the end effector, a position and orientation information is determined at a different point in time. The control unit 14 is connected to the screen 5 as well as to an interface unit 17 which allows the transfer of information determined by the control unit 14 to at least a peripheral device 18, such as a computer, a data storage, and/or the X-ray apparatus 4.

Figure 3:
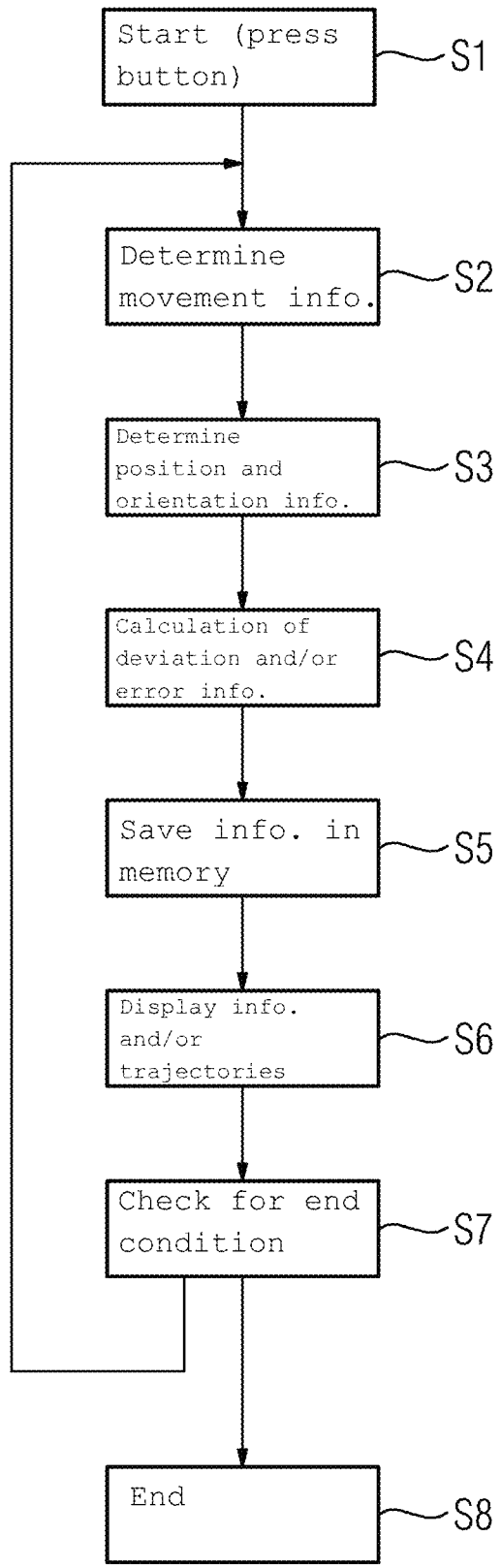
FIG. 3 depicts a schematic view on an information display on a screen according to an embodiment.

In FIG. 3, a flow diagram of the method for tracking the hand guided robot 1 is depicted.

The method is started (S1) by the operator, e.g., by pushing a button. After starting of the tracking method, a movement information of each joint is determined (S2). From the determined movement information of each joint and from the kinematic and dynamic model, an absolute position of the end effector 10 inside the operational volume 11 is determined (S3). The position and orientation information is stored in the memory 16 of the control unit 14. If one or more position and orientation information of previous iterations are stored in the memory, a displacement trajectory is determined.

Afterwards, in act S4, if a displacement trajectory has been determined in act S3, a deviation information of the current position and/or a displacement trajectory from the target trajectory is calculated. It is also possible that an error information for the determined position and orientation information is calculated based on the kinematic and dynamic model. The error information may be based on correction factors or on tolerances for the individual manipulator 6 or for a misalignment of axis or for an axis offset. In act S5, the displacement trajectory is saved in the memory 16 of the control unit 14. Also, the deviation information and/or an error information may be stored in this act. In act S6, the position and orientation information as well as the deviation information and/or the error information are displayed on the screen 5. Additionally, it is also possible that the target trajectory and/or the displacement trajectory are displayed on the screen. It is also possible that, in this act, a new image data set recorded by the X-ray apparatus 4 of the patient 2 is displayed on the screen 5 as well, on which the position and orientation information, the deviation information, the error information, or a combination thereof may be overlaid, based on the registration between the image data set and the coordinate system in which the tracking is performed.

In act S7, an end condition is checked. An end condition may be fulfilled, for instance, if the operator has pressed a respective button for ending the tracking of the hand-guided robot or if no movement has been detected within a fixed number of subsequent iterations. If the end condition applies, the method moves forward to the end act (S8). If the end condition is not met, the method begins another iteration at act S2 determining the next information of each joint. The time needed for one iteration is the time defining the temporal and/or spatial resolution of the displacement trajectory.

Figure 4:
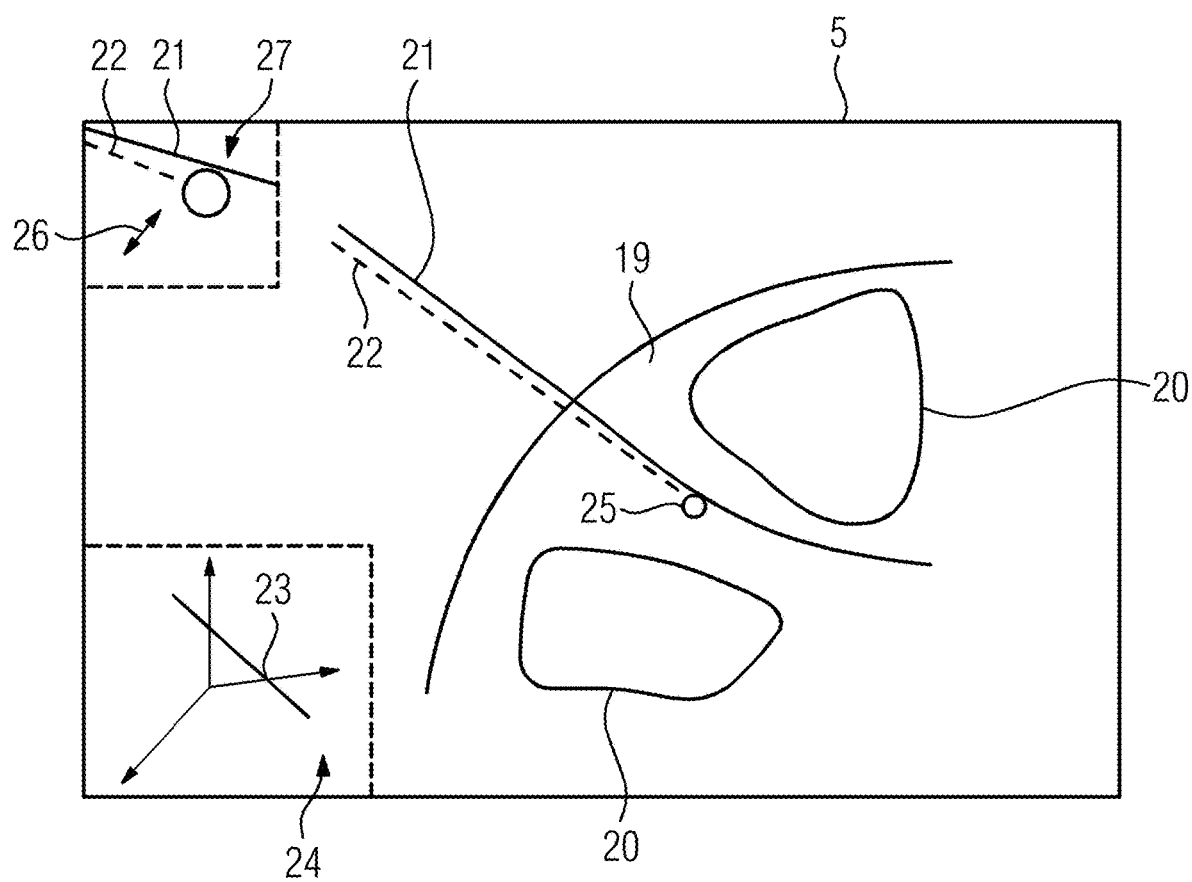
FIG. 4 depicts a schematic diagram of an embodiment of a method.

In FIG. 4, an example of the information shown on the screen 5 is depicted. The information shown on the screen 5 includes an image data set of the patient 2 recorded by the X-ray apparatus 4, from which a target anatomy 19 for the minimal invasive intervention is selected and depicted on the screen 5. This target anatomy 19 may include areas 20, (e.g., organs or blood vessels), that should not be harmed during the minimal invasive intervention. In addition to the anatomy 19, a target trajectory 21, which may have been planned before, as well as the displacement trajectory 22 are shown on the screen 5. The current position, (e.g., of the tip 12 of the end effector 10), is shown by the circle 25, in which, for example, the radius for the circle 25 corresponds to the error information and the position of the circle 25 corresponds to the current position and orientation information. It is noted that in a three dimensional depiction of the information, the circle 25 may be a sphere.

Additionally, it is possible that a deviation information 26 corresponding to the deviation between the displacement trajectory 22 and the target trajectory 21 is shown in a separate area 27, (e.g., on a magnified scale), on the screen 5. An orientation information 23 corresponding to the current position and orientation information of the end effector 10 is shown in a separate area 24 of the screen 5. If the frequency in which the position and orientation information as well as the deviation information and/or the error information are obtained is high enough, a real time monitoring of the position and orientation of the end effector 10 during the minimally invasive intervention is possible, in particular, using a pre-interventional image data set as background for the depiction. In particular, in case of x-ray imaging, no or only few image data sets may be required to be acquired during the intervention itself, reducing the irradiation of the patient while still receiving detailed position and orientation information from the model. A frequency in which the image data set describing the anatomy 19 of the patient 2 is obtained may be different from the frequency in which the position of the end effector 10 is determined using the kinematic and dynamic model. In particular, no inter-interventional image data sets are acquired.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for tracking a hand-guided robot, the hand-guided robot comprising a control unit and a manipulator coupled to an end effector, wherein the manipulator comprises a plurality of joints and links and the end effector is manually displaceable within an operational volume, the method comprising:

determining, by the control unit, at least one movement information of each joint during and/or after an at least partially manual displacement of the end effector; and determining, by the control unit, a position and orientation information of the end effector inside the operational volume during and/or after the displacement of the end effector using the determined movement information of each joint and a software-based kinematic and dynamic model of the manipulator stored in a memory of the control unit.

2. The method of claim 1, wherein the software-based kinematic and dynamic model is an absolutely accurate model.

3. The method of claim 1, wherein the movement information of a joint comprises an information on a rotational movement of the joint, a translational movement of the joint, a torque applied to the joint, a force applied to the joint, or a combination thereof.

4. The method of claim 1, wherein the software-based kinematic and dynamic model describes a geometry of the manipulator and at least one property of at least one joint or link of the manipulator, and wherein the at least one property comprises a friction of a joint, a flexibility of a joint, a hysteresis of a joint, a backlash of a joint, an elasticity of a link, or a combination thereof.

5. The method of claim 1, wherein the control unit determines a displacement trajectory of the end effector during displacement by determining the position and orientation information at different points in time during displacement.

6. The method of claim 5, wherein the control unit calculates, at each point in time, a deviation information respectively describing a deviation between the displacement trajectory and a target trajectory, which is stored in the memory of the control unit.

7. The method of claim 6, further comprising:
displaying one or more of the deviation information, the displacement trajectory, or the target trajectory on a screen connected to the control unit;
transferring one or more of the deviation information, the displacement trajectory, or the target trajectory via an interface unit of the control unit to at least one peripheral device; or
a combination thereof.

8. The method of claim 7, further comprising:
displaying an image data set of a workpiece or a patient on the screen.

9. The method of claim 5, further comprising:
displaying the displacement trajectory on a screen connected to the control unit;
transferring the displacement trajectory via an interface unit of the control unit to at least one peripheral device; or
a combination thereof.

10. The method of claim 9, further comprising:
displaying an image data set of a workpiece or a patient on the screen.

11. The method of claim 1, wherein the control unit calculates an error information for each determined position and orientation information based on the software-based kinematic and dynamic model.

12. The method of claim 11, further comprising:
displaying the error information on a screen connected to the control unit;
transferring the error information via an interface unit of the control unit to at least one peripheral device; or
a combination thereof.

13. The method of claim 1, wherein the end effector is a biopsy needle, an ablation electrode, or an endoscope,
wherein a medical minimally invasive intervention on a patient is surveyed, or
wherein the biopsy needle, the ablation electrode, or the endoscope is used as end effector, and the medical minimally invasive intervention on the patient is surveyed.

14. The method of claim 1, wherein the hand-guided robot is a serial arm robot with at least six joints and six degrees of freedom.

15. A hand-guided robot comprising:
a manipulator coupled to an end effector, wherein the manipulator comprises a plurality of joints and links and the end effector is manually displaceable within an operational volume; and
a control device configured to:
determine at least one movement information of each joint during and/or after an at least partially manual displacement of the end effector; and
determine position and orientation information of the end effector inside the operational volume during and/or after the displacement of the end effector using the determined movement information of each joint and a software-based kinematic and dynamic model of the manipulator stored in a memory of the control device.

16. A non-transitory computer readable medium storing thereon a computer program, which, when executed by a control unit of a hand-guided robot, causes the control unit to at least perform:
determine at least one movement information of each joint of the hand-guided robot during and/or after an at least partially manual displacement of an end effector of the hand-guided robot; and
determine position and orientation information of the end effector inside an operational volume during and/or after the displacement of the end effector using the determined movement information of each joint and a software-based kinematic and dynamic model of a manipulator of the hand-guided robot stored in a memory of the control unit.

\* \* \* \* \*